United States Patent [19]
Garigipati et al.

[11] Patent Number: 6,075,166
[45] Date of Patent: Jun. 13, 2000

[54] PHOTOLYTICALLY CLEAVABLE ENCODING AND LINKING AGENTS FOR USE IN COMBINATORIAL CHEMISTRY

[75] Inventors: Ravi Shunker Garigipati; Jerry Leroy Adams, both of Wayne, Pa.

[73] Assignee: SmithKline Beecham Corporation, Philadelphia, Pa.

[21] Appl. No.: 08/414,855

[22] Filed: Mar. 31, 1995

[51] Int. Cl.$^7$ ........................ C07C 311/29; C08B 11/193; C08F 112/08
[52] U.S. Cl. ........................ 564/89; 526/294; 526/346; 526/347.1; 526/347.2; 536/30; 536/31; 536/43; 536/44; 546/172; 546/338; 549/49; 549/75; 564/84; 564/85; 564/86
[58] Field of Search ........................ 564/89, 84, 85, 564/86; 536/30, 31, 43, 44; 526/294, 346, 347.1, 347.2; 546/172, 338; 549/75, 491

[56] References Cited

U.S. PATENT DOCUMENTS

| | | | |
|---|---|---|---|
| 4,474,600 | 10/1984 | Aya et al. | 564/89 |
| 4,971,620 | 11/1990 | Jikihara et al. | 564/89 |
| 5,514,696 | 5/1996 | Murugesan et al. | 514/380 |
| 5,523,464 | 6/1996 | Kinoshita et al. | 560/140 |
| 5,618,825 | 4/1997 | Baldwin et al. | 514/317 |

FOREIGN PATENT DOCUMENTS

| | | | |
|---|---|---|---|
| 54-86596 | 7/1979 | Japan | 560/140 |
| WO 94/10135 | 5/1994 | Japan . | |

OTHER PUBLICATIONS

Hamada, et al., J. Am. Chem. Soc., 108, pp. 140–145 (1986).
Hamada, et al., Tetrahedron Letters, vol. 30, No. 32, pp. 4241–4244 (1989).

*Primary Examiner*—Peter O'Sullivan
*Attorney, Agent, or Firm*—Dara L Dinner; Stephen Venetianer; Charles M Kinzig

[57] ABSTRACT

The present invention is to novel photochemically cleavable aryl sulfonamides of the formula

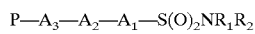

wherein $R_1$ and $R_2$ are independently selected from optionally substituted alkyl, arylalkyl or heteroarylalkyl;

$A_1$ is an aryl or heteroaryl moiety;

$A_2$ is a linking agent is an aryl, heteroaryl, arylalkyl, heteroaryl alkyl, or an alkyl, wherein the alkyl moiety in the arylalkyl, heteroaryl alkyl, or alkyl group is optionally interrupted one or more times independently by oxygen, $NR_3$, sulfur or an amide group;

$R_3$ is alkyl;

$A_3$ is an electron rich aryl or heteroaryl moiety having an $E_{1/2}$ potential of 0.5 to 2.0 and which moiety is capable of forming an exciplex;

P is a solid support.

Another aspect of the present invention is to the novel use of these photolytically cleavable aryl sulfonamides in combinatorial chemistry synthesis, for use in non-sequential encoding, as a tagging agent.

Another aspect of the present invention is to the novel use of these photolytically cleavable aryl sulfonamides in combinatorial chemistry synthesis, as a linking agent which is bound to a solid support, and upon photolytic cleavage will provide a free amine of the desired final products, i.e. the use of sulfonamides for the solid phase synthesis of amines.

9 Claims, No Drawings

PHOTOLYTICALLY CLEAVABLE ENCODING AND LINKING AGENTS FOR USE IN COMBINATORIAL CHEMISTRY

FIELD OF THE INVENTION

The present invention is to a method of determining specific compounds produced by combinatorial means by use of a non-sequential, non-binary tagging system.

BACKGROUND OF THE INVENTION

Recently, a new field of "combinatorial chemistry" has emerged which produces a "chemical library" having large numbers of members belonging to it. The library may contain peptides, or small molecular weight compounds. Expanding the positions and number of building blocks used in these libraries rapidly increases the number of possible members. As these members will be screened for various activities the deciphering or determination of the particular molecule of interest becomes a necessity. One therefore needs an efficient method to decipher the contents of the resulting library.

Many methods have been reported in the literature by which individual members of combinatorial libraries may be encoded by "tagging molecules" (hereinafter "tags"). Thus, a single molecular structure synthesized on a resin bead, for instance, is uniquely defined by a series of other, readily detectable, molecules, also bound to a resin. Individual beads are treated to release their library member, often by a process which does not displace the tag, and following identification of this compound as an "active" in a biological screen, the tags are released and analyzed to deduce the identity of the "hit". To allow for maximum diversity in a library it is critical that the chemistry used to introduce the tags is tolerated by a wide range of functionality. Thereby, introduction of the tagging molecule does not lead to undesired elaboration of the library structure, or alternatively, place limits upon the chemistry used to construct the library. Similarly, if the tag is removed prior to the library member, that conditions for removal of the tag does not destroy or react in some manner with the designed molecule.

There remains a need for the development of a molecular tag that is easy to use, readily available for detection by known means, that is stable to all the reaction conditions required to build the library, and is stable to all the conditions necessary to cleave the individual components of the library. The present invention provides for such an encoding process.

SUMMARY OF THE INVENTION

The present invention is to novel photochemically cleavable aryl sulfonamides of the formula

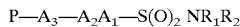

wherein
  $R_1$ and $R_2$ are independently selected from optionally substituted alkyl, arylalkyl or heteroarylalkyl;
  $A_1$ is an aryl or heteroaryl moiety;
  $A_2$ is a linking agent is an aryl, heteroaryl, arylalkyl, heteroaryl alkyl, or an alkyl, wherein the alkyl moiety in the arylalkyl, heteroaryl alkyl, or alkyl group is optionally interrupted one or more times independently by oxygen, $NR_3$, sulfur or an amide group;
  $R_3$ is alkyl;
  $A_3$ is an electron rich aryl or heteroaryl moiety having an $E_{1/2}$ potential of 0.5 to 2.0 and which moiety is capable of forming an exciplex;
  P is a solid support.

Another aspect of the present invention is to the novel use of these photolytically cleavable aryl sulfonamides in combinatorial chemistry synthesis, as a sequential encoding, or tagging agent.

Another aspect of the present invention is to the novel use of these photolytically cleavable aryl sulfonamides in combinatorial chemistry synthesis, as a linking agent which is bound to a solid support, and upon photolytic cleavage will provide a free amine of the desired final products, i.e. the use of sulfonamides for the solid phase synthesis of amines.

DETAILED DESCRIPTION OF THE INVENTION

It is well known that aryl sulfonamides are very robust and stable to most common organic transformations. It has been reported that aryl sulfonamides can be cleaved photolytically in the presence of an electron rich arene (Hamada, et al., *J. Am. Chem. Soc.*, 1986 (108) 140). One aspect of the present invention is the discovery of a versatile tagging system that uses aryl sulfonamides as photolytically cleavable molecular tags for use in combinatorial chemistry.

Another aspect of the present invention is the novel use of the amine function of the sulfonamide moiety as a means for the non-sequential identification of a series of chemical process steps for a desired molecule. The photolytic cleavage will upon irradiation cleave the sulfonamide bond, hence allowing determination of the amine components, by means of detection well known to those skilled in the art.

Another aspect of the present invention is the novel use of these photolytically cleavable sulfonamides as a linking agent to allow easy removal of the desired final product from the solid support by photolytic cleavage of the sulfonamide bound, hence freeing the amine library of compounds.

These photochemical strategies are extremely useful in combinatorial chemistry because of their simple workup and purification, their use under conditions which are readily adapted to solid phase synthesis work, and they are orthogonal to standard protection chemistry.

In the instant process, the low chemical reactivity of the sulfonamide insures a high degree of compatibility with chemistry generally performed on the resins, or solid support.

One aspect of the present invention are the photolytically cleavable aryl and heteroaryl sulfonamides of the formula:

wherein
  $R_1$ and $R_2$ are independently selected from optionally substituted alkyl, arylalkyl or heteroarylalkyl;
  $A_1$ is an aryl or heteroaryl moiety;
  $A_2$ is an aryl, heteroaryl, arylalkyl, heteroaryl alkyl, or an alkyl group, wherein the alkyl moiety in the arylalkyl, heteroaryl alkyl, or alkyl group is optionally interrupted one or more times independently by oxygen, $NR_3$, sulfur or an amide group;

$R_3$ is alkyl;

$A_3$ is an electron rich aryl or heteroaryl moiety having an $E_{1/2}$ potential of 0.5 to 2.0, and which is capable of forming an exciplex.

These aryl sulfonamides may be bound to a soluble or solid support (P) giving the formula:

$$P-A_3-A_2-A_1-S(O)_2 NR_1R_2 \qquad (II)$$

wherein $A_1$ to $A_3$, $R_1$ and $R_2$ are as defined above for formula (I).

The solid supports for use herein are those commonly used in combinatorial chemistry, such as the various resin beads, cellulose, glass beads etc. Preferably the solid support is a resin bead, such as the Merrifield, Wang or TentgaGel line of beads, preferably of polystyrene origin. It is recognized that virtually all types of polymer beads can be functionalized for use by simple chemical reactions. Generally, the functionality of the beads, such as on a polystyrene bead, is a hydroxyl moiety, generally attached to a phenyl ring from the polymer resin, i.e. a Merrifield resin. This entire functionalized resin is what is referred to by the term P, as used for instance, in formula II. The functionalized moiety is used as is or chemically altered to provide an attachable site to either an electron rich aryl or heteroaryl moiety capable of forming an exciplex ($A_3$) or the remaining $A_1$ or $A_2$ functionalities of the sulfonamide complex.

In formula (I) the aryl sulfonamide is bound through a chain which may be an aryl, an arylalkyl, a heteroaryl, a heteroarylalkyl, or an alkyl group. Each of these alkyl containing groups may be branched or straight chain, and the chain may further be interrupted one or more times independently by an oxygen, $NR_3$, sulfur or amide moiety.

Suitably, the $A_2$ is selected from aryl, heteroaryl, arylalkyl, heteroarylalkyl, —$(CR_4R_5)_n$—, —$XR_6$—, —R6X—, —$R_6$—X—$R_6$—, X—$R_6$—X—$R_6$—, —$R_6$X—$R_6$—X, or —X—$R_6$—X—$R_6$—X—, wherein $R_6$ is aryl, heteroaryl, arylalkyl, heteroarylalkyl, or $(CR_4R_5)m$ ; and wherein X is independently selected from oxygen, $NR_3$, sulfur or an amide linkage; $R_4$ and $R_5$ are independently hydrogen, or alkyl; n is an integer from 1 to 10; m is 0 or an integer from 1 to 10. It is preferable that the total chain length of $A_2$ not exceed 10 atoms. For example, in the figure below the $A_2$ moiety has 4 atoms numbered , 2 carbon atoms in the aryl ring, an oxygen atom and a methylene group, between the $A_1$ and the $A_3$ donor group. The remaining atoms in the $A_2$ aryl ring are not counted towards the 10.

It is further recognized that any of the $A_1$, $A_2$, or $A_3$ moietites may be additionally substituted with any group which is chemically inert and does not under chemical reaction during the combinatorial process of building a library of compounds. The $A_3$ moiety, is clearly recognized as being required to be substiuted with groups which provide an oxidation potential for transfer of the electron. Generally, this will be alkoxy moieties which are also chemically unreactive for the processes contemplated herein.

A suitable example of a compound of Formula (I) is described below, wherein the ring labeled $A_1$ is the aryl moiety, the ring $A_2$ an aryl moiety, and the the $A_3$ group is an alkoxy, preferably a methoxy, substituted benzyloxy moiety (wherein n is 1 to 4).

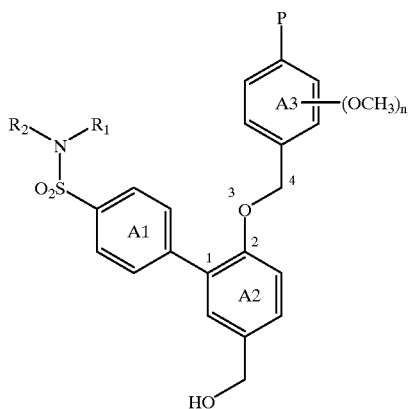

Other compounds exemplified herein which correspond to a compound of Formula (I) include,

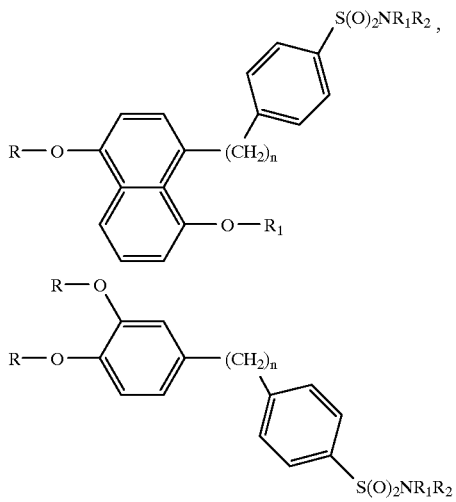

wherein R is alkyl , or arylalkyl; and n is 1 to 10

It is recognized that in order to use the amine functionality ($NR_1R_2$) as an encoding agent the $R_1$ and $R_2$ moieties which are independently selected from optionally substituted alkyl, arylalkyl or heteroarylalkyl, also require substiutents which are functionally inert, and chemically unreactive. They further must be distinguishable if they are to be detected by mass spectronomy. Suitably, such groups will include halogens, particularly fluorine, deuterium, alkyl, ethers or aromatic ring systems, such as phenyl or napthyl. Other groups could include cyano, alcohols, and sulfonamides if circumstances permit. Clearly, moieites which are reactive, such as carbonyl containing groups, i.e. esters, amide, ketones, aldehydes are not likely candidates for use, although under the right circumstances it may be possible to utilize such.

Generally for use herein the following defintions apply:

"halo"—all halogens, that is chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl, naphthyl or anthracenyl ring systems.

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclicalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "aralkyl" or "heteroarylalkyl" or "heterocyclicalkyl" is used herein to mean $C_{1-10}$ alkyl as defined above attached to an aryl, heteroaryl or heterocyclic moiety, as also defmed herein, unless otherwise indicated.

Another aspect of the present invention are the photolytically cleavable aryl and heteroaryl sulfonamides of the formula:

P—$A_2$—$A_1$—$S(O)_2$ $NR_1R_2$     (III)

wherein
$R_1$ and $R_2$ are independently selected from optionally substituted alkyl, arylalkyl or heteroarylalkyl;
$A_1$ is an aryl or heteroaryl moiety;
$A_{2'}$ is a bond, an aryl, heteroaryl, arylalkyl, heteroaryl alkyl, or an alkyl group, wherein the alkyl moiety in the arylalkyl, heteroaryl alkyl, or alkyl group is optionally interrupted one or more times independently by oxygen, $NR_3$, sulfur or an amide group;
$R_3$ is alkyl;
P is a soluble or solid state support; wherein Formula (III) is in solution with an $A_3$ moiety which $A_3$ moiety is an electron rich aryl or heteroaryl moiety having an $E_{1/2}$ potential of 0.5 to 2.0 and is capable of forming an exciplex.

It has been found that the functionality which becomes an exciplex need not be physically attached to the arylsulfonamide moiety but only need be in solution with sulfonamide in order to transfer energy to the sulfonamide bond for cleavage. There are many potential advantages of using an electron rich moiety in solution, one of which may be reduced synthetic costs, i.e. less steps, to build the arylsulfonamide group attached to the resin.

The $A_3$ moiety herein is generally referred to as an electron rich moiety which is capable of forming an exciplex. The term exciplex is a well known term to those of skill in the art and is an important type of interaction which is the formation of a relatively long-lived molecular complex of excited species. Many molecules that do not interact significantly in their ground states appear to form reasonably stable complexes when excited. The complexes are called excimers or exciplexes. Thus, an exciplex is produced by the interaction of an excited molecule with a ground-state molecule of a different chemical species, hence the term excited complex (rather than the same chemical species which is an excimer or excited dimer). The exciplexes have a fixed stiochiometric composition, usually 1:1. The nature of the bonding in exciplexes is clearly dependent on the presence of electronic excitation, and charge-transfer stabilization is important in exciplexes. Excited species are also usually both better electron donors and better electron acceptors than in their the ground states.

Upon excitation light is absorbed by the electron rich aromatic (an aromatic compound with an oxidation potential in the range of an $E_{1/2}$ from about 0.5 to 2.0, preferably from about 1.05 to about 1.55), and it forms an exciplex with the electron deficient sulfonamide and an electron transfer occurs to the sulfonamide bond, and cleavage occurs between the $S(O)_2$ and the $NR_1R_2$ group. This process differs from photolysis of a molecule which the species not only absorbs the energy but is also the same species which will undergo a reaction, such as release of a photon. An example of an electron rich aromatic is veratrole, or the aromatic exciplexs listed as fluorophor's in Table II of Hamada et al., *J. Am. Chef Soc.*, 108, p 140–145 (1986), and Hamada et al., Tetrahedron Letters, Vol. 30, No. 32, pp 4241–44 (1989) whose disclosure are incorporated by reference herein in their entirety.

It should be noted that the transfer of the electron to the sulfonamide bond does not require that the electron rich aromatic donor be physically attached to the sulfonamide containing moiety. The electron donor, may for instance, merely be in solution, such as illustrated in compounds of Formula (III).

This interaction is illustrated generally in Scheme I, below, wherein the aryl sulfonamide complex of the formula $A_1$—$S(O)_2NR_1R_2$ is generically disclosed, and is irradiated under appropriate conditions to allow formation of an exciplex but the electron rich moiety, in solution or alternatively, connected physically to the aryl sulfonamide such as indicated in compounds of Formula (I). This irradiation will cleave the bond between the $S(O)_2$ and the $NR_1R_2$ group allowing for recovery of the free amine, either as a tagging or encoding agent or as a library of compounds.

Scheme I

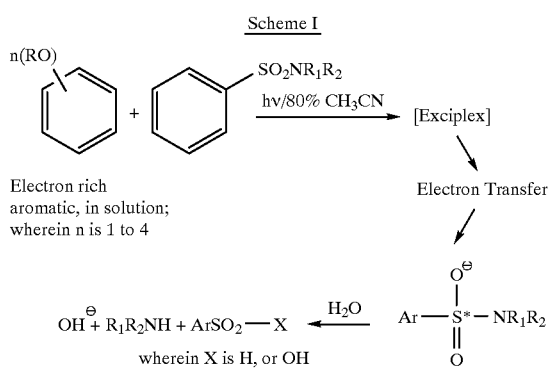

If the irradiation is carried out in an aqueous "polar" solvent, such as water and/or THF, $CH_3CN$, or EtOH, the cleavage of the sulfonamide occurs to yield the amine. A reducing agent such as a hydride, $NaBH_4$, $BH_3.NH3$, $NH_2NH_2$, ascorbic acid, or $BH_3$.t-butylamine complex, is preferably added to yield an efficient cleavage.

It should be noted that when the electron rich moiety is on the sulfonyl side of the aryl sulfonamide, and not in solution nor on the amine component the donor functionality, i.e. the electron rich moiety should not directly link with the acceptor component, i.e. the $A_1$ or aryl moiety attached directly to the sulfonyl group. The cleavage of the sulfonamide bond is most efficient when there is a separation of 1 to 3 atoms. The longer the separation, the greater the irradiation time, or increased intensity of the light source may be needed.

For instance, when the arylsulfonamide shown below is irradiated with NaBH4 with veratrole present in the solution, clean photolysis occurred. As shown below, in Scheme II, the phenyl ring having the $A_1$ notation is the acceptor molecule and corresponds to the $A_1$ group as described herein. The phenyl ring having the D notation is meant to describe a situation when this is the donor group. When R is H or methoxy the arylsulfonamide cleavage is not efficient and requires an electron rich moiety in solution, such as veratrole to work. When the ring having an E notation is substituted with additional moieties such as alkoxy this aryl ring will, in fact, become an electron rich moiety capable of becoming an electron donor. Alternatively, if at least one atom, such as a carbon atom, separates the D and $A_1$ ring then when the D ring has sufficient electron rich moieties (an oxidation potential of 0.5 to 2.0) it may function as a donor group.

Scheme II

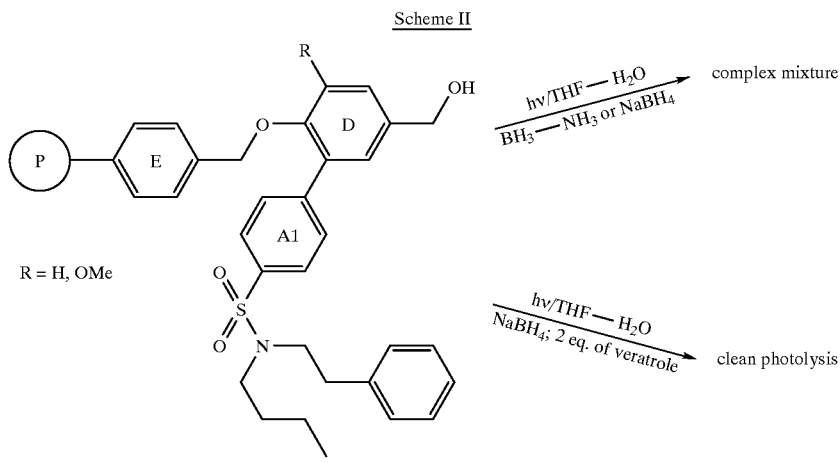

When the donor group is integral with the sulfonyl portion of the molecule, clean photolysis was achieved with out the addition of veratrole in solution. This is illustrated below then the $A_1$ group is separated by 4 atoms (noted as 1 to 4 in the schematic) from the donor group (D) ring. The phenyl ring having the methanol group is for instance, a position of attachment for the library or ligand component. This schematic also shows the functionalized attachment the benzyl alcohol group of to the resin or solid support (P).

Scheme III

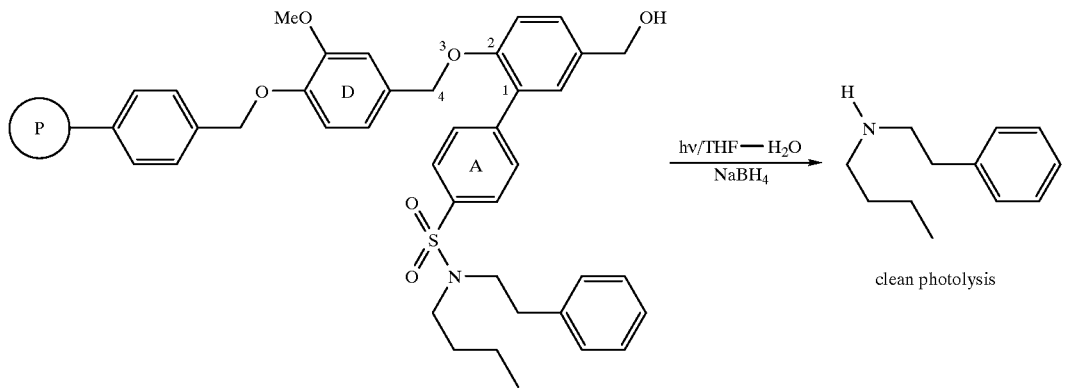

clean photolysis

It is believed that the mechanism for the cleavage of the arylsulfonamides occurs as illustrated in the scheme below.

Scheme IV

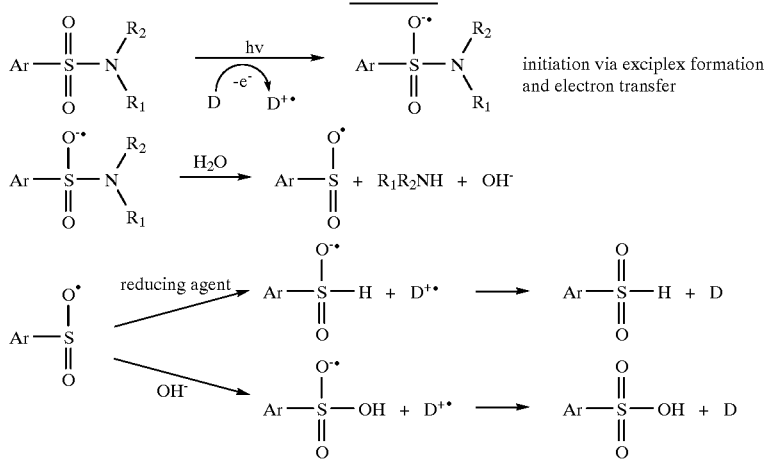

initiation via exciplex formation and electron transfer

Another aspect of the present invention are the novel aryl sulfonamides where the electron rich aryl or heteroaryl moiety is on the amine side of the sulfonamide moiety. In other words, the donor molecule can in fact become a part of the amine group which is used in the detection and encoding portion of the molecule. Such compounds correspond to the formula:

$$A_{2'}—A_1—S(O)_2—NR_1R_2 \quad (IV)$$

wherein the $A_{2'}$ and $A_1$ moieties correspond to those described above for Formula (III). One of $R_1$ and $R_2$ however, must be an electron rich aryl or heteroaryl moiety having an $E_{1/2}$ potential of 0.5 to 2.0 and capable of forming an exciplex, and there needs to be a linker A2 wherein $A_2$ is an aryl, heteroaryl, arylalkyl, heteroaryl alkyl, or an alkyl group, wherein the alkyl moiety in the arylalkyl, heteroaryl alkyl, or alkyl group is optionally interrupted one or more times independently by oxygen, $NR_3$, sulfur or an amide group. Generally an alkyl chain will suffice to connect the electron rich aryl moiety to the nitrogen. As with compounds of Formula (I) the longer the chain or linker ($A_2$) between the donor group and the nitrogen, the higher the intensity of irradiation or the longer the time of irradiation may be needed to cleave the sulfonamide bond. Generally a linkage of 1 to 10 atoms is suitable, with 1 to 3 preferable.

Similarly, as noted above for compounds of Formula (I) and (III), these compounds can be attached to the solid support (P), to form the compounds of formula (V):

$$P—A_{2'}—A_1—S(O)_2—NR_1R_2 \quad (V)$$

wherein the $A_{2'}$, and $A_1$ moieties correspond to those described above for Formula (IV).

Shown below, are 2 sets of 11 groups which can code for 121 unique compounds by MS (mass redundancy >0.90). Mass ranges of the amines are from 271 to 631. The groups can be alternated either as the X group or the R group as desired. The examples of suitable encoding agents, shown as formula (VI), using these two sets of 11 groups are after cleavage from the sulfonamide moiety, i.e. as the free amine.

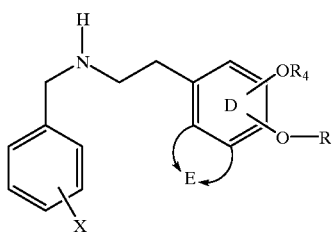

(VI)

wherein D is the electron rich aryl moiety or donor molecule as the term is alternatively used herein and the D ring may be composed of one or more ring systems, such as where E optionally forms one or more saturated or unsaturated 5–7 membered rings, and which rings be optionally comprise one or more heteroatoms selected from O/N/S, with the phenyl ring to which it is attached; it is also noted that the $OR_4$ and OR moieties may be substituted on any of the rings therein in the D moiety. It is recognized that for purposes herein, the substituent groups are shown on the phenyl ring for ease of description. Suitable groups corresponding to an E moiety, are napthyl, anthracene, and indoles, for instance. The $R_4$ moietiy is an alkyl, preferably a methyl; and X is $CH_3$, $CD_3$, $C_2H_5$, $C_3H_7$, $C_4H_9$, $C_5H_{11}$, $C_6H_{13}$, $C_7H_{15}$, $C_8H_{17}$, $C_9H_{19}$, and $C_{10}H_{21}$.

The R is group is selected from (note that the molecular formula is shown to the left of each schematic)

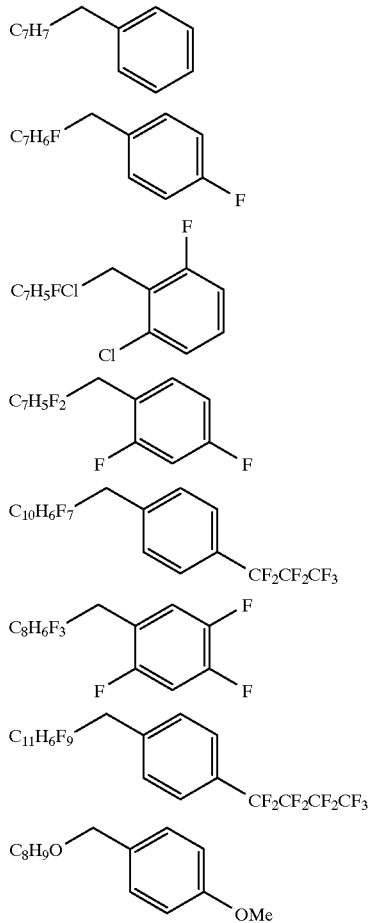

-continued

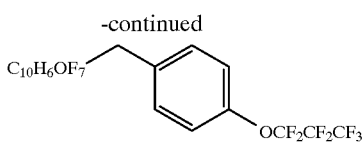

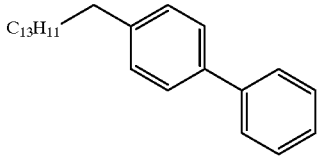

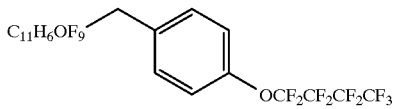

The position of the substituent on the R group, i.e. F, or methoxy for instance is not relevant to the total molecular weight and hence all the various positional isomers are also specifically exemplified herein.

While the compound noted above has, on the benzyl moiety specifically two substituents, one of which is methoxy and the other the O-R group, the compound could also be recognized as being the following group as well.

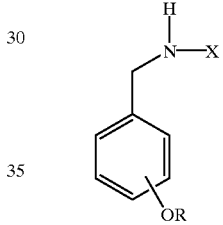

It should therefore, be readily recognized by one of skill in the art, that the groups chosen are highly variable and that the present invention is not so limited as to only those coding agents specifically exemplified herein. The choice of groups for coding as determined by mass spec, will generally be those reagents whose combination provides for unique molecular weights, for instance, halogens, such as fluorine or combinations of suitable halogens, deuterimun, aryls, and ethers. Alternatively, combinations of substituents which provide for unique chromatographic properties, i.e. retention times, are alternatives which are clearly contemplated as being within the scope of this invention.

The present invention is also to an orthogonally coupled appropriately substituted (4-sulfonamido) aryl boronic acid, preferably wherein the aryl is a phenyl, illustrated as compound 1 in Table II below. These phenyl boronic acid are coupled to an appropriately brominated polystyrene resin, such as those illustrated as compounds 2 and 3 in this table, in concert with an ongoing combinatorial library synthesis. A very wide variety of phenyl boronic acids 1 can be prepared in three steps simply by varying R and R' groups. It is also recognized by one of skill in the art that many other solid supports, commonly used in the solid supported synthesis, such as the Tentagel™ line of resins, may be used instead of the polystyrene resins, such as the Merrifield or Wang resins.

Table II:

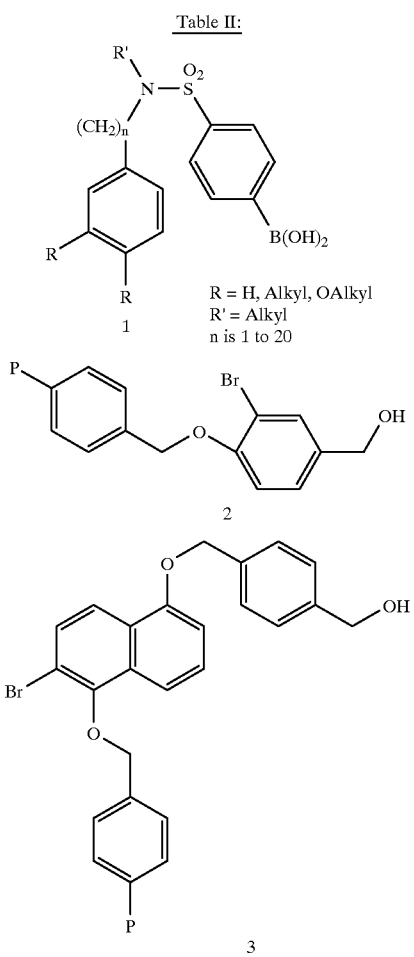

The appropriately substituted aryl boronic acids described above, and illustrated in 1(R=alkyl)-Scheme IV below are shown as being efficiently coupled to the brominated solid supports, as 2-Scheme IV under the standard Suzuki coupling conditions. As one would expect similar reaction rates, all the required tags can be coupled in one step.

Standard Suzuki coupling conditions involve coupling an aryl halide or triflouromethanesulfonate (triflate) with an aryl or vinyl boronic acid in the presence of a Palladium (0) catalyst. The coupling is usually carried out in benzene (or higher aromatic hydrocarbons), glyme (or other related ethers), acetonitrile, THF etc. at approximately 80–100° C. in the presence of a base such as $K_2CO_3$ or KF.

Alternatively, a mono substituted aryl sulfonamide 1(R=H)-Scheme IV can be coupled to the solid support 2-Scheme IV, and the resulting resin bound sulfonamide can be alkylated under Mitsunobu reaction conditions. A standard Mitsunobu reaction, as illustrated in step (b) is carried out between any alcohol and a moiety of moderate acidity, such as phenol, sulfonamide etc. The alcohol is usually activated with a phosphine such as triphenylphosphine in THF, N-methylpyrrolidine or benzene and the acidic partner and dialkylazodicarboxylate are added and the reaction is complete in about 12 or more hours.

Scheme IV

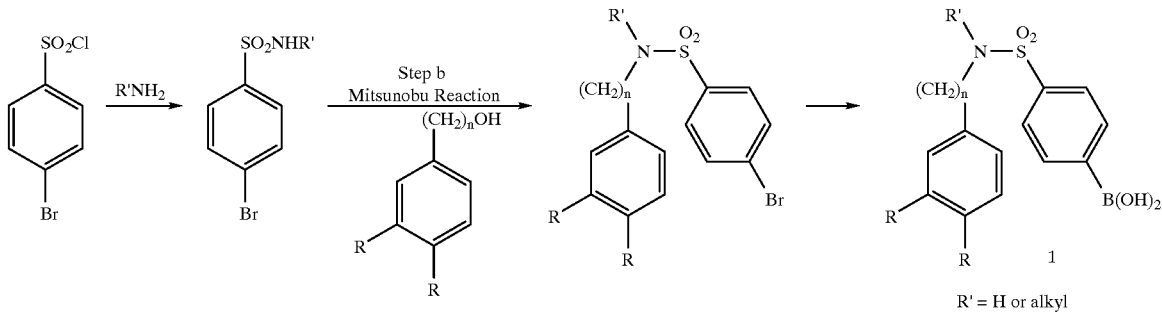

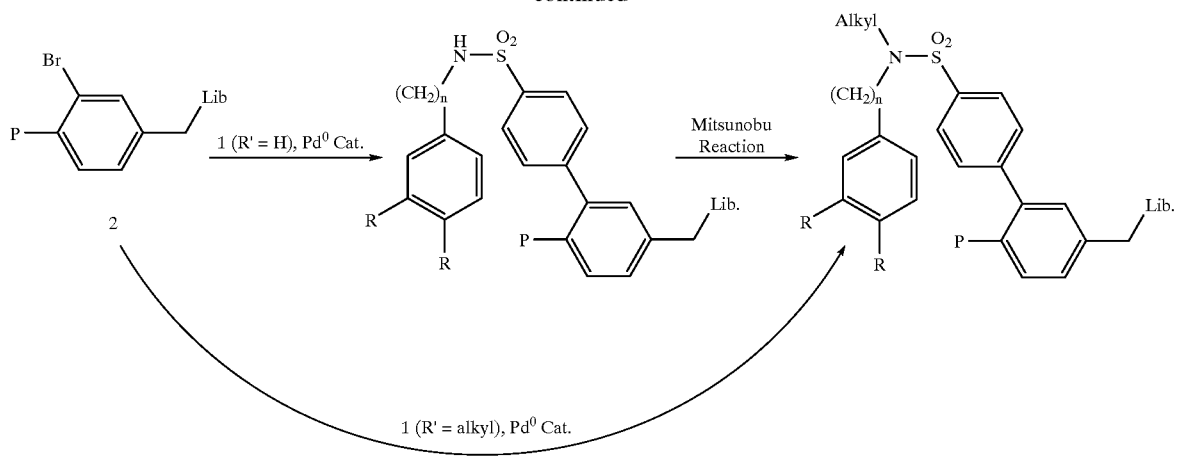

While the coupling reaction of the resin to the arylsulfonamide component, in this scheme has the library directly attached to the resin through an aryl group, the invention is not so limited thereby, and the library attachment may be added wherever practical and through as many atoms as is deemed necessary or desirable for ease of removal.

It is also recognized that the basic resin or solid support (P), generally is considered mono-functional, i.e. has one functional group, such as an alcohol or an amine. It is possible to utilize a bi-functional resin such that one of the functionalities ties in the library component, and the other functionality is used for the tagging component.

Once the individual components of the library have been recovered from the solid support by any means other than photolytic cleavage, such as by acid or base induced cleavage, or using oxidative or reductive conditions, the tag can be released by photolysis. The resulting amines can by identified by mass spectrometry (CIMS, ESI (+) or (−) FIA) or by any other suitable means, such as electron capture GC.

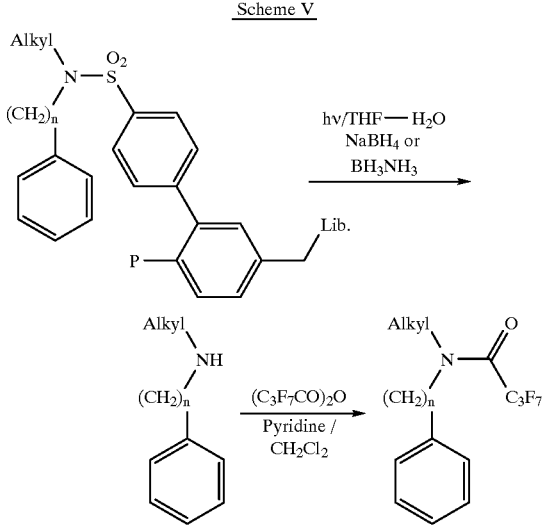

Scheme V

Derivatization of the free amine may be done (Scheme VI), to increase sensitivity of the negative ion detection, and to remove the signal from the lower molecular weight interferences which may be present. Under current sensitivity from generally available mass spec., a single bead detection is possible. For instance, using the reaction described above in Scheme V, wherein the free amine is derivatized to the amide the MS detection threshold was for DCL/NH$_3$ [42 pmols for amine; and 23 pmol for the amide]; using ESI (+) FIA detection was [840 fmol for amine and 450 fmol for amide].

A photochemical cleavage of an arylsulfonamide attached to a solid support (R) is shown below in Scheme VI. In this example the first step is to construct a bifunctional resin (2-Scheme-VI) which allows for the construction of the the aryl sulfonamide and an addtional functionality which can be used to attach the library memebers. Thus reaction of a chloromethylated polystyrene (Merrifield resin) under basic conditions (NaOMe, K$_2$CO$_3$ etc.) with a phenol having 2 addtional functional groups affords 2-Scheme-VI. A transition metal mediated biaryl coupling reaction, such as the Suzuki reaction, is used to attach the aryl-metal partner to form 7-Scheme-VI. In this example the arylboronic acid 6-Scheme-VI is prepared in 3 steps from the comercially available 4-bromophenylsulfonyl chloride. Photolysis of 2-Scheme-VI under suitable conditions cleaves the amine component. The reaction as previously described is best controlled with an additional reducing agent. In this particular instance, when NaBH$_4$ was used a 20% yield occurred; with BH$_3$-NH$_3$, a 78% yield; and with BH$_3$-NH$_2$-t-Bu, a 40% yield was achieved. The complete removal of the amine, requires several hours, however depending upon the general reaction conditions the cleavage may range from several minutes to several days. Alternatively, the resin 7-Scheme-VI can be reduced to the corresponding alcohol (8-Scheme-VI) by LAH to yield a "tagged Wang resin".

Preferably irradiation is from about 300 nm to about 400 nm, more preferably from about 320 nm to about 350 nm.

Scheme VI

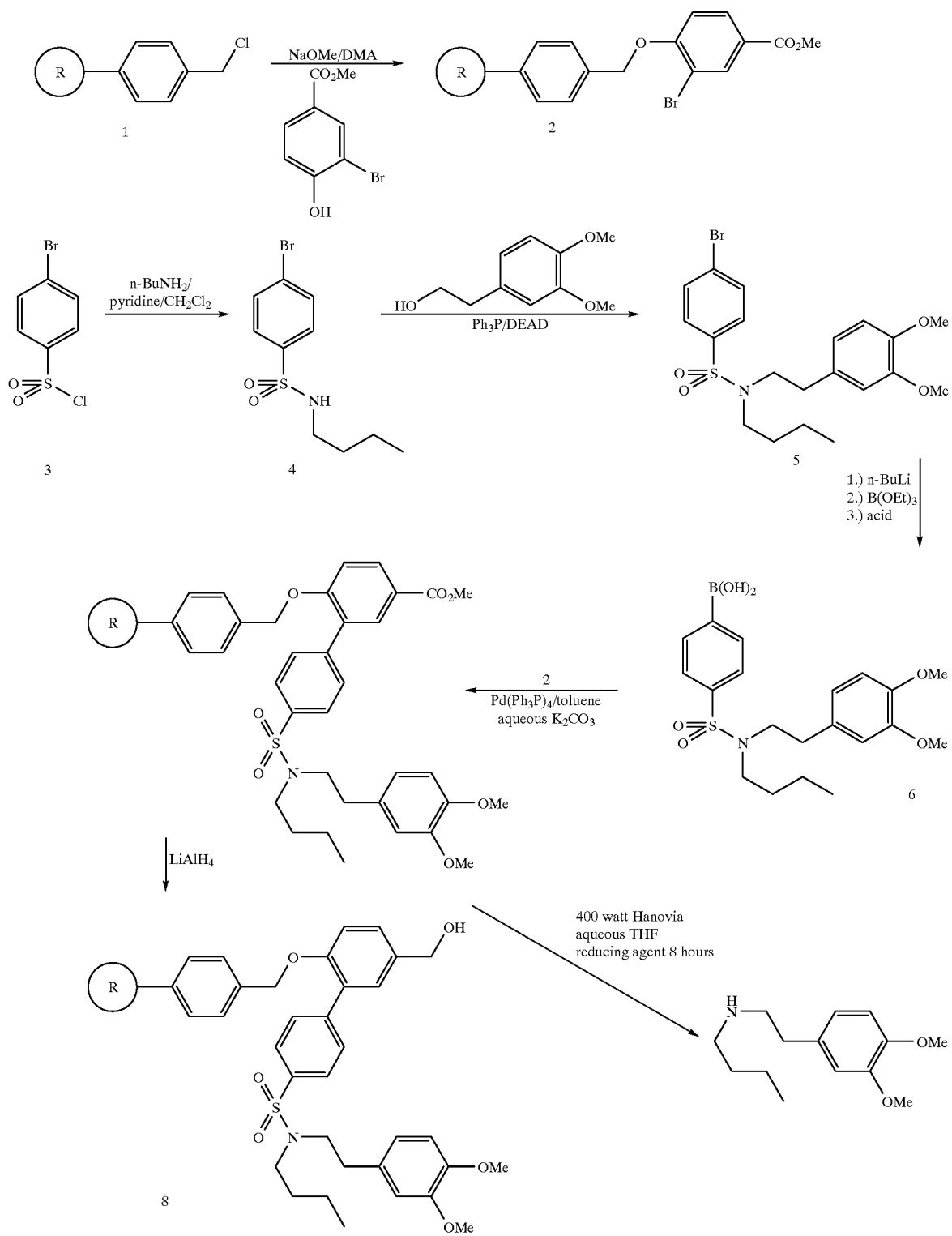

The utility of the arylsulfonamides as an encoding tool stems from their ability to uniquely identify a single member of a large library. This makes the arylsulfonamides a strongly desired tool as it is suitable for use in SAR work (structure-activity relationships) and requires no deconvolution of the library, a time consuming and expensive process.

While binary coding, such as described by Still et al; in WO 94/08051 is a very efficient process for exceedingly large libraries, a non-binary method should suffice for libraries generally under 10,000. Sequential coding has traditionally required as many tags as the maximum number of regents in any one step. The non-sequential, non-binary methods requires as many tags as reagents X steps. Therefore, use of this non-sequential, non-binary method as described herein, coupled to an easily available detection systems, such as negative ion MS , or electron capture GC allows the synthetic chemist to focus on the preparation of the desired ligands, and place emphasis for deconvolution on the analytical chemist, hence separating the activities of the personnel often involved in such processes. The practicality of this potentially allows a technician, to use an inexpensive technique to decode in an accurate, and rapid fashion, a library of compounds. This particular encoding technique provides for simple chemistry, in high yield, with the chemistry orthogonal to the library chemistry.

Aryl sulfonamides are particularly attractive as an encoding agents because the tags are chemically inert, their removal is by photochemical means, and there is a high sensitivity of detection of the tag as there is an equimolar amount of the tag component being produced as is the library component (or ligand). Further, resins encoding for the first step would require no additional effort for use in library synthesis. When one desires to encode for two steps, approximately 100 to 120 tags may be envisioned which will uniquely identify members of 3 step libraries of 1,000. Coupling this with MS of a library member it will uniquely identify most compounds in a 3–4 step library of 10,000.

The use of aryl sulfonamide as a means to synthesis amine combinatorial libraries is also advantageous as the general synthesis as shown herein will produce a primary or secondary amine. The only primary requirement to use the aryl sulfonamides for synthesis of amines is that an electron rich donor linker must be inserted either on the sulfonyl side of the molecule or be in solution to facilitate cleavage from the resin. The limitations of using the arylsulfonamides to produce amine combinatorial libraries would be that an alternative encoding strategy is necessary.

A general example of a combinatorial synthesis of a 1000 member library by steps $A_1$, $B_1$ and $C_1$ using $R_1$ and $R_2$ for encoding of the aryl sulfonamide is shown in Scheme VII below. In this example the idenity of the $C_1$ component is not encoded as the resins are not mixed following the addition of the last library member.

Scheme VII

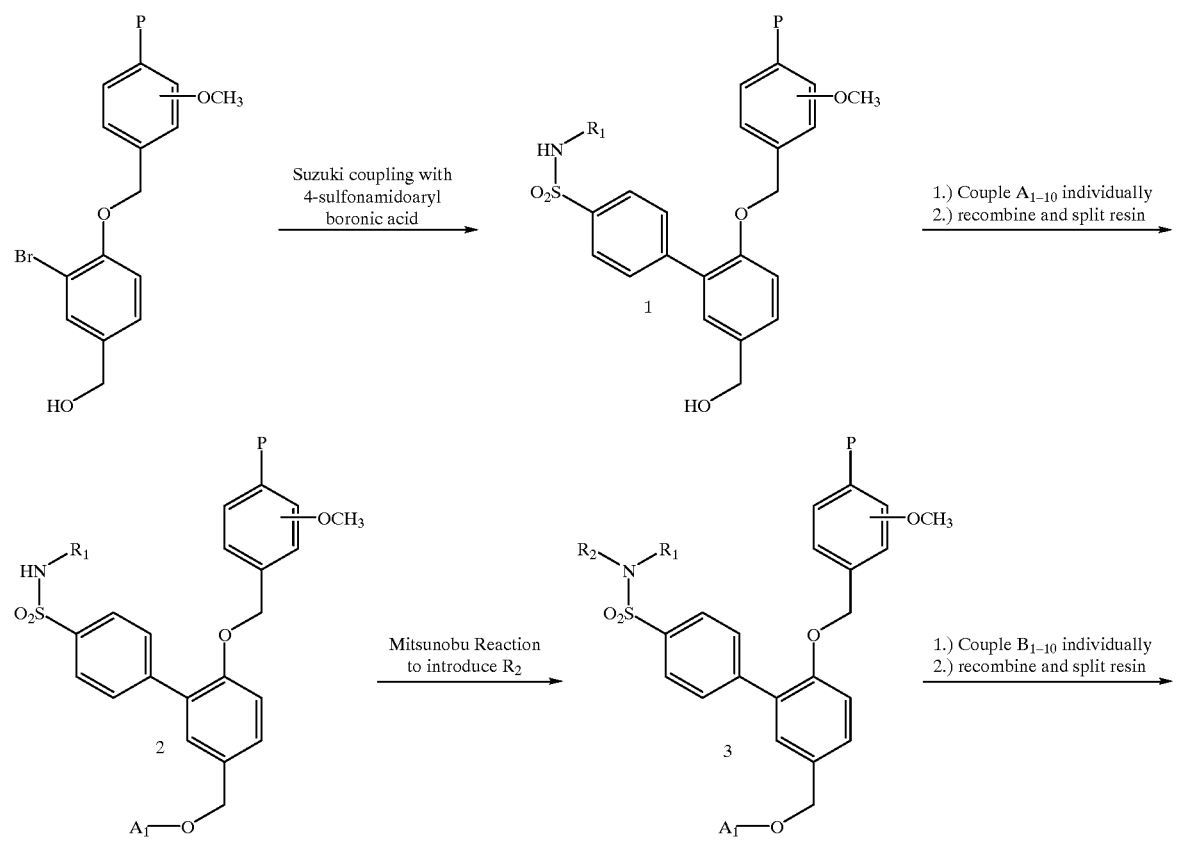

-continued

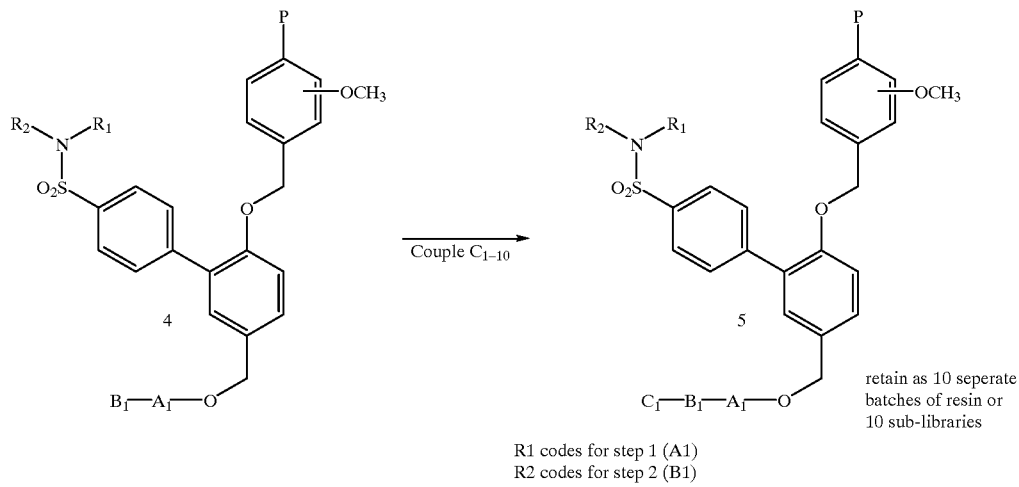

R1 codes for step 1 (A1)
R2 codes for step 2 (B1)

The compound 5-Scheme VII (shown below in schemeVIII) is reacted in any means commonly acceptable to those skilled in the art to release the ligand, i.e. the compound, $A_1$—$B_1$—C and the remaining solid support bound aryl sulfonamide (6-Scheme VIII) is subsequently tag must be performed on individual beads when this invention is used for the decoding of the identity of library members. By using 10 different appropriately chosen $R_1$ and $R_2$ groups the library compenents in the example of Scheme VII can be uniquely identified.

Scheme VIII

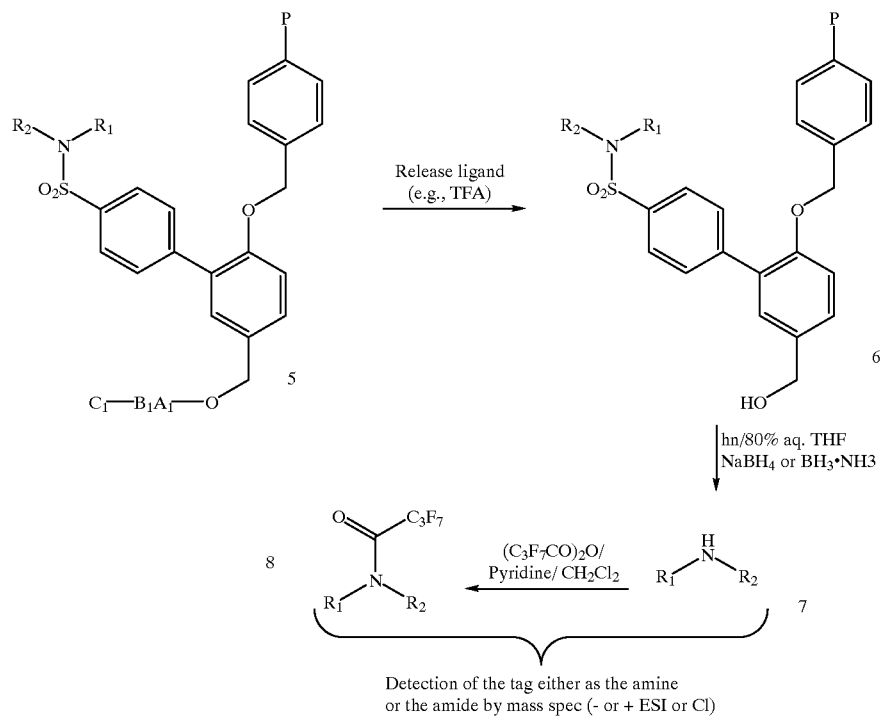

Detection of the tag either as the amine
or the amide by mass spec (- or + ESI or Cl)

reacted to remove the amine, 7-Scheme VIII which is identified directly or following derivatization to enhance detection of the tag It is recognized that the aryl sulfonamide bond could be cleaved prior to release of the ligand, if so desired. It is also recognized that the cleavage and testing of the library ligand and the release of the corresponding amine An example of a particular photochemical synthesis and cleavage of an aryl sulfonamide for use an encoding technique is shown in Scheme IX below.

Scheme IX
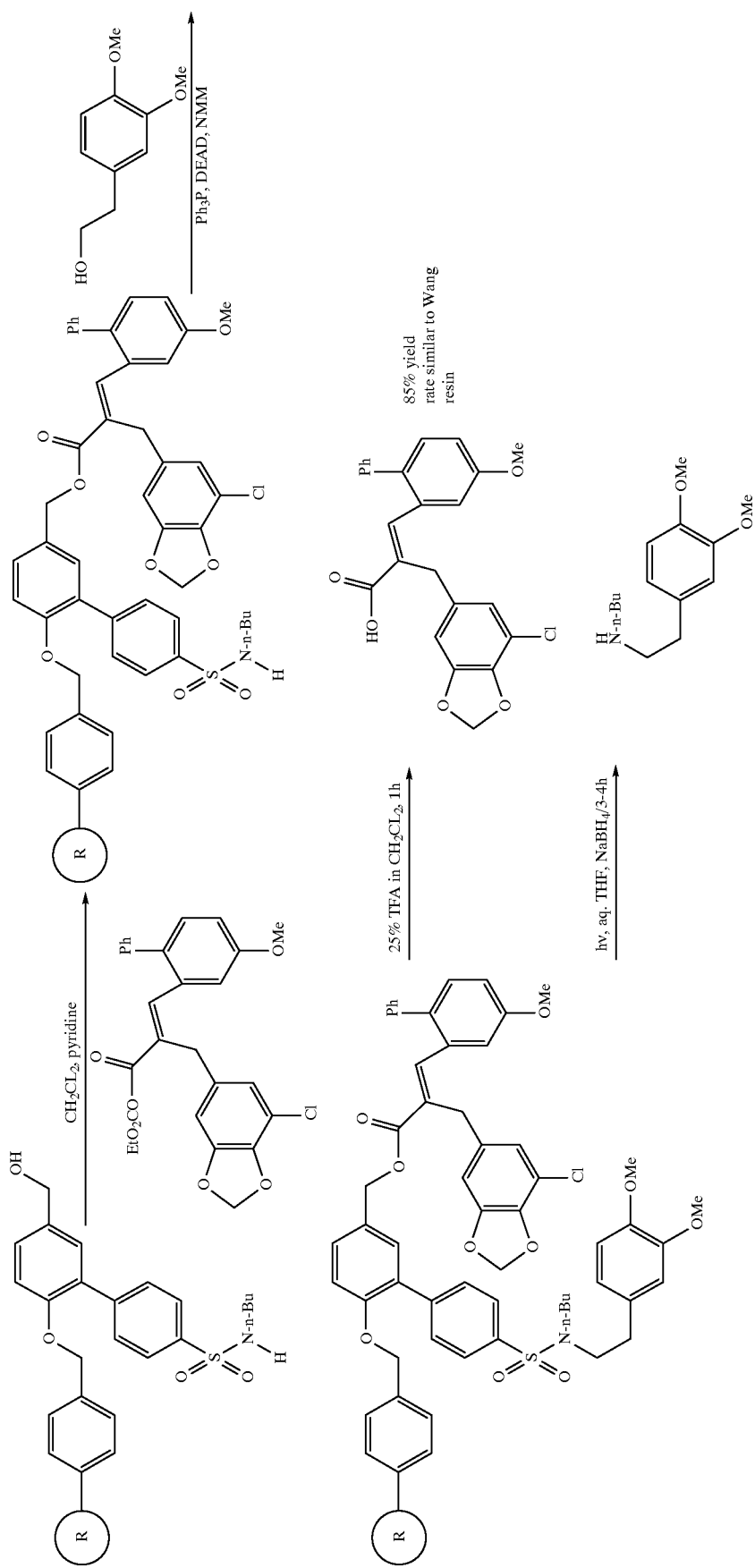

One particularly convenient application of the aryl sulfonamide resins for coding would be the preparation of a number of precoded aryl sulfonamide resins for use in the combinatorial synthesis (Scheme X). These premade encoding resins, which might be either acid stable or acid labile, would be used to as the starting resins for combinatorial synthesis and would require no encoding if only one chemical step was to be encoded.

are to be construed as merely illustrative and not a limitation of the scope of the present invention in any way. The embodiments of the invention in which an exclusive property or privilege is claimed are defined as follows.

What is claimed is:

1. A composition of the formula $$P—A_3—A_2—A_1—S(O)_2NR_1R_2$$

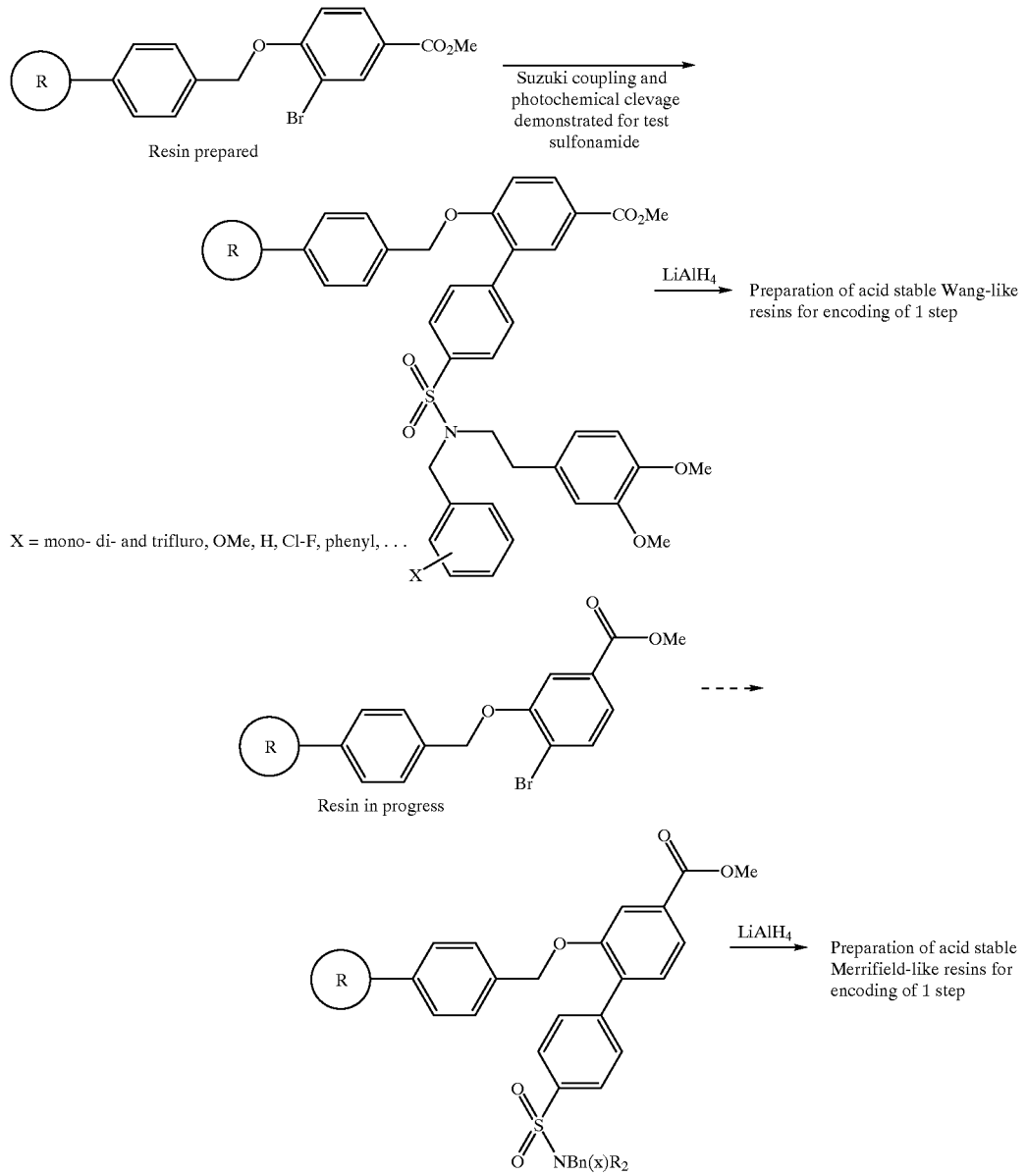

Scheme X

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein wherein P is a soluble or solid support;

$R_1$ and $R_2$ are independently selected from optionally substituted alkyl, arylalkyl or heteroarylalkyl;

$A_1$ is an aryl moiety;

$A_2$ is a linking agent wahich is an aryl, arylalkyl, —$(CR_4R_5)_n$—, —$XR_6$—, —$R_6X$—, —$R_6$—X—$R_6$—, X—R₆—X—R₆—, —R₆X—R₆—X, or —X—R₆—X—R₆—X—;

R₃ is alkyl;

R₆ is aryl, arylalkyl, or (CR₄R₅)ₘ;

X is independently selected from oxygen, NR₃, sulfur or an amide linkage;

R₄ and R₅ are independently hydrogen or alkyl;

n is an integer from 1 to 10;

m is 0 or an integer from 1 to 10;

A₃ is an electron rich aryl moiety having an E₁/₂ potential of 0.5 to 2.0 and which moiety is capable of forming an exciplex.

2. The composition compound according to claim 1 wherein the A₂ moiety is alkoxy or methylene.

3. The composition compound according to claim 1 wherein the A₃ moiety has an E₁/₂ of 1.05 to about 1.55.

4. The composition according to claim 3 wherein the A₃ moiety is selected from anthracene, phenyl, or a naphthyl moiety each substituted one to four times independently by an alkoxy group.

5. The composition compound according to claim 1 wherein the A₁ moiety is phenyl.

6. The composition according to claim 1 wherein said support is a functionalized resin which contains a phenyl alkyl hydroxy group for attachment of the electron rich A₃ moiety capable of forming an exciplex.

7. The composition according to claim 1 wherein A₃—A₂—A₁— is defined as

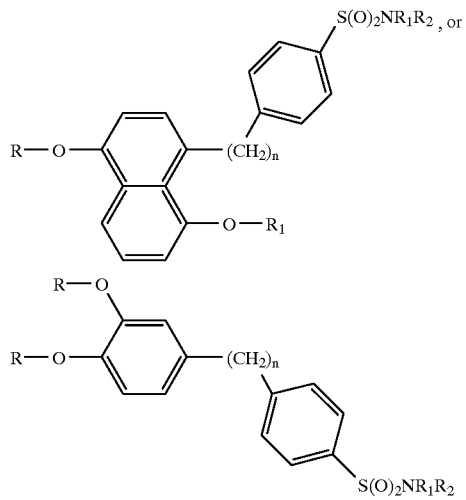

wherein

R is alkyl, or arylalkyl;

R₁ and R₂ are independently selected from optionally substituted alkyl, arylalkyl or heteroarylalkyl; and n is an integer having a value of 1 to 10.

8. The compound according to claim 1 wherein the NR₁R₂ component is

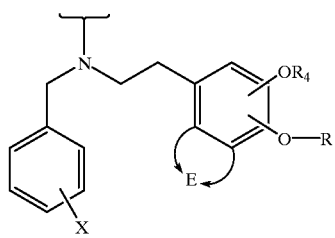

wherein R₄ is an alkyl;

E optionally forms one or more saturated or unsaturated 5–7 membered rings, optionally comprising one or more heteroatoms selected from N/O or S, with the phenyl ring to which it is attached; and R is

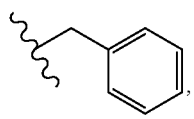

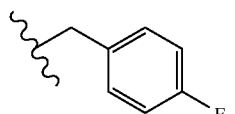

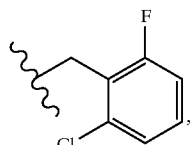

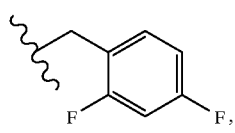

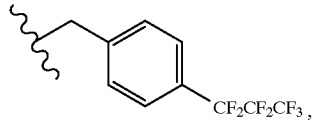

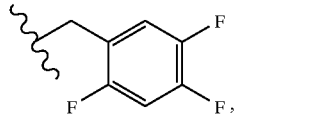

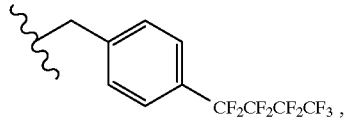

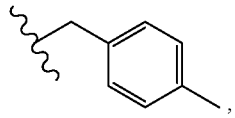

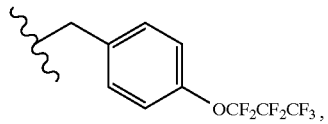

-continued
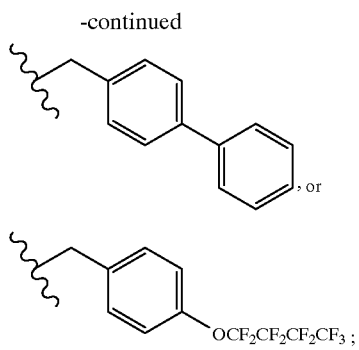, or
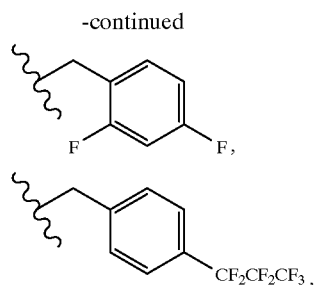
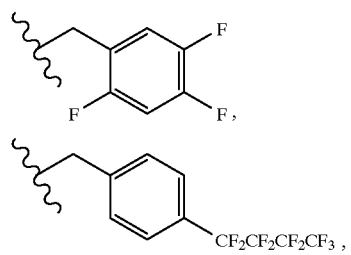
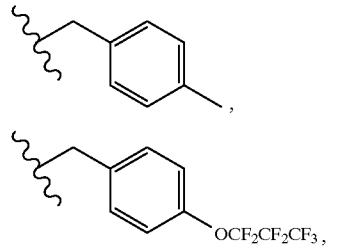
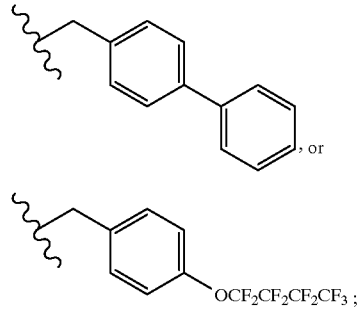
and X is selected from $CH_3$, $CD_3$, $C_2H_5$, $C_3H_7$, $C_4H_9$, $C_5H_{11}$, $C_6H_{13}$, $C_7H_{15}$, $C_8H_{17}$, $C_9H_{19}$, or $C_{10}H_{21}$.
9. The compound according to claim 1 wherein the $NR_1R_2$ component is
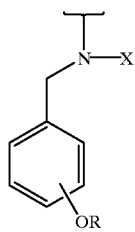
and R is
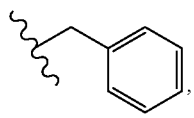,
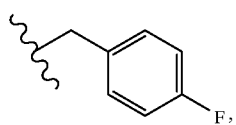,
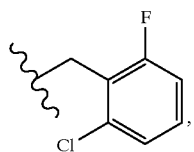,
and X is selected from $CH_3$, $CD_3$, $C_2H_5$, $C_3H_7$, $C_4H_9$, $C_5H_{11}$, $C_6H_{13}$, $C_7H_{15}$, $C_8H_{17}$, $C_9H_{19}$, or $C_{10}H_{21}$.
\* \* \* \* \*